United States Patent
Mills et al.

(10) Patent No.: US 11,439,342 B2
(45) Date of Patent: Sep. 13, 2022

(54) ORAL FOOD CHALLENGE MEAL FORMULATIONS

(71) Applicant: Reacta Biotech Limited, Manchester (GB)

(72) Inventors: Clare Mills, Altrincham (GB); Anuradha Balasundaram, Manchester (GB); Carol Ann Costello, Manchester (GB); Ivona Baricevic-Jones, Stockport (GB); Martin Wickham, Manchester (GB)

(73) Assignee: Reacta Biotech Limited, Manchester (GB)

( * ) Notice: Subject to any disclaimer, the term of this patent is extended or adjusted under 35 U.S.C. 154(b) by 0 days.

(21) Appl. No.: 16/347,753

(22) PCT Filed: Dec. 5, 2016

(86) PCT No.: PCT/GB2016/053829
§ 371 (c)(1),
(2) Date: May 6, 2019

(87) PCT Pub. No.: WO2018/104691
PCT Pub. Date: Jun. 14, 2018

(65) Prior Publication Data
US 2019/0328308 A1    Oct. 31, 2019

(51) Int. Cl.
*A61K 9/00*     (2006.01)
*A61B 5/00*     (2006.01)
*A23L 25/00*    (2016.01)
*A23L 33/115*   (2016.01)
*A23L 29/212*   (2016.01)

(52) U.S. Cl.
CPC .............. *A61B 5/411* (2013.01); *A23L 25/30* (2016.08); *A23L 29/212* (2016.08); *A23L 33/115* (2016.08)

(58) Field of Classification Search
CPC .......... A61B 5/411; A23L 33/115; A23L 9/10; A23L 29/212; A23L 35/00; A23L 9/12; A61N 5/411; A23V 2200/304
See application file for complete search history.

(56) References Cited

U.S. PATENT DOCUMENTS

| 2015/0343075 A1* | 12/2015 | Raff ...................... A61P 43/00 424/489 |
| 2016/0030289 A1* | 2/2016 | Walser ................ A61K 9/4875 424/452 |
| 2016/0088849 A1* | 3/2016 | Nickel .................. A21D 2/263 426/540 |

FOREIGN PATENT DOCUMENTS

WO    2016020336 A1    2/2016

OTHER PUBLICATIONS

Odijk et al. Double-blind placeno-controlled challenges for peanut allergy the efficiency of blinding procedures and the allergenic activity of peanut availability in the recipes, Allergy 2005: 60: 602-605. (Year: 2006).*
Czaja-Bulsa et al., The natural history of IgE mediated wheat allergy in children with dominant gastrointestinal symptoms, Allergy, Asthma & Clinical Immunology 2014, 10:12. (Year: 2014).*
EFSA, Opinion of the Scientific Panel on Dietetic Products, Nutrition and Allergies on a request from the Commission related to a notification from AAC on wheat-based maltodextrins pursuant to Article 6, paragraph 11 of Directive 2000/13/EC; The EFSA Journal, May 2007 487, 1-7. (Year: 2007).*
International Search Report and Written Opinion for corresponding PCT Application No. PCT/GB2016/053829, dated Jul. 3, 2017, 14 pp.
Cochrane, et al., "Development of a standardized low-dose double-blind placebo-controlled challenge vehicle for the EuroPrevall project," Allergy, vol. 67, 2012, pp. 107-113, XP055286521.
Ronteltap, et al., "Sensory testing of recipes masking peanut or hazelnut for double-blind placebo-controlled food challenges," Allergy, vol. 59, 2004, pp. 457-460, XP055286528.
Czaja-Bulsa et al., "The natural history of IgE mediated wheat allergy in children with dominant gastrointestinal symptoms," Allergy, Asthma & Clinical Immunology, Biomed Central Ltd., London, UK, vol. 10, No. 1, Feb. 26, 2014, XP021178727, ISSN: 1710-1492-10-12, 7 pp.
Ballmer-Weber, B. K., et al., How much is too much? Threshold dose distributions for 5 food allergens, The Journal of Allergy and Clinical Immunology, vol. 135, No. 4, pp. 964-971, Apr. 2015.
Bock, S. A., et al., Double-blind, placebo-controlled food challenge (DBPCFC) as an office procedure: a manual, The Journal of Allergy and Clinical Immunology, vol. 82, No. 6, pp. 986-997, Dec. 1988.
Ingelfinger, F. J., et al., Gastrointestinal Allergy, The New England Journal of Medicine, vol. 241, No. 9, pp. 337-340, Sep. 1, 1949.
Niggemann, B., et al., Pitfalls in double-blind, placebo-controlled oral food challenges, Allergy, 62, pp. 729-732, Jul. 2007.
Sampson, H. A. et al., Standardizing double-blind, placebo-controlled oral food challenges: American Academy of Allergy, Asthma & Immunology—European Academy of Allergy and Clinical Immunology PRACTALL consensus report, The Journal of Allergy and Clinical Immunology, vol. 130, No. 6, pp. 1260-1274, Dec. 2012.
Vassilopoulou, E. et al., Evaluation and standardisation of different matrices used for double-blind placebo-controlled food challenges to fish, Journal of Human Nutrition and Dietetics, 23, pp. 544-549, Oct. 2010.

(Continued)

*Primary Examiner* — Susan T Tran
(74) *Attorney, Agent, or Firm* — Shumaker & Sieffert, P.A.

(57) ABSTRACT

This invention relates to kits including novel oral food challenge meal formulations. In particular, the invention also relates to kits including novel oral food challenge meal formulations, wherein the placebo dose formulation is indistinguishable from non-placebo dose formulations.

15 Claims, 2 Drawing Sheets

(56) References Cited

OTHER PUBLICATIONS

Vlieg-Boerstra, B. J. et al., Development and validation of challenge materials for double-blind, placebo-controlled food challenges in children, The Journal of Allergy and Clinical Immunology, 113, pp. 341-346, Feb. 2004.

Mackie, A. et al., High fat food increases gastric residence and thus thresholds for objective symptoms in allergic patients, Molecular Nutrition & Food Research, vol. 56, Issue 11, pp. 1708-1714, Nov. 2012.

* cited by examiner

ORAL FOOD CHALLENGE MEAL FORMULATIONS

This application is a national stage application under 35 U.S.C. § 371 of PCT Application No. PCT/GB2016/053829, filed Dec. 5, 2016. The entire contents of the PCT Application No. PCT/GB2016/053829 is incorporated herein by reference in their entirety.

This invention relates to kits including novel oral food challenge meal formulations. In particular, the invention also relates to kits including novel oral food challenge meal formulations, wherein the placebo dose formulation is indistinguishable from non-placebo dose formulations. The invention also relates to novel oral food challenge meal formulations, to methods of using the kits and the novel oral food challenge meal formulations and to a use of an additive compound to improve the properties of an oral food challenge meal formulation. In particular, the invention relates to novel oral food challenge meal formulations having improved taste and/or texture masking properties for the allergen contained in the formulation.

BACKGROUND

Oral food challenges are generally considered to be the gold-standard for diagnosis of food related adverse reactions to foods, including IgE-mediated reactions, especially when performed in a double-blind, placebo-controlled fashion[1]. The original concept was described in 1949 at which time it was suggested that food should be given in such a way that the patient is unaware of its nature[2].

Oral food challenges are usually undertaken to confirm whether an individual has a clinical allergy and can drive treatment plans including elimination diets and food avoidance, as well as prescription of rescue medication should a patient inadvertently consume a problem food[3]. There have been several position papers on diagnosis of food allergy which have focussed primarily on the clinical aspects of undertaking double blind placebo controlled food challenges (DBPCFC), culminating in the recently published PRACTALL consensus paper[4].

Much effort has focussed in the clinical community on harmonising clinical protocols and stopping criteria but little consideration has been given to standardisation of the agents and food vehicles used for food challenges, or for dose verification. A key attribute of a food allergen challenge is to blind or mask the flavour and texture of the "active" allergenic food, to provide a placebo dose (without allergen) and active dose (containing allergenic ingredient) where the patient cannot tell which dose they are being given. This has resulted in a plethora of different approaches and recipes, includes various cooked and baked products, cakes and milks shakes, and different methods to assess the efficacy of blinding, including triangle testing, a sensory test used by the food industry to compare products[5-7].

It is generally accepted that allergenic foods should be used in their usual edible form and this was the approach that was adopted in the EuroPrevall project. In the EuroPrevall project, a chocolate dessert base formulation was developed which was capable of blinding a variety of commercially available dry powdered food ingredients and is an ambient shelf-life stable product by virtue of its low water activity[8,9]. This was done to ease the issues of cost-effective shipping and shelf-life requirements for the multi-centre, transnational project. The matrix has been used to collect a variety of challenge data including peanut, hazelnut, celery spice (celeriac) and fish powder[10]. It is reconstituted at the point of use by addition of potable water, stored chilled (2-8° C.) and used within 24 h of rehydration. To date challenge meal formulations have generally fallen short of the requirement of blinding or masking the flavour and texture of the "active" allergenic food. For example, the EuroPrevall project describes that, although hazelnut allergen was successfully masked, the same could not be said for celeriac as 30/37 panellists (i.e. 81%) without nose clips and 27/35 panellists (i.e. 77%) were able to correctly identify the difference between the placebo sample and the 'high-allergen' sample. The panellists in this study reported the 'high-allergen' dessert as having a more 'grainy', less 'smooth' texture and less 'sweet', more 'bitter' taste and, consequently, less 'chocolate' flavour.

OBJECTS OF THE INVENTION

It is an aim of the present invention to provide an oral food challenge meal formulation having taste-masking properties for an allergen present in the formulation.

It is also an aim of the present invention to provide an oral food challenge meal formulation having texture-masking properties for an allergen present in the formulation.

It is also an aim of the present invention to provide an oral food challenge meal formulation having taste-masking properties such that a challenge meal formulation containing an allergen is indistinguishable from a challenge meal formulation in which the allergen is absent (i.e. a placebo challenge meal formulation).

It is also an aim of the present invention to provide an oral food challenge meal formulation having texture-masking properties such that a challenge meal formulation containing an allergen is indistinguishable from a challenge meal formulation in which the allergen is absent (i.e. a placebo challenge meal formulation).

The present invention achieves one or more, e.g. all, of the above listed aims.

SUMMARY OF THE DISCLOSURE

In accordance with the present invention there is provided a kit comprising:

a challenge meal formulation comprising no food allergen (i.e. a placebo challenge meal formulation); and a challenge meal formulation comprising allergen, wherein the allergen is present in the challenge meal formulation in an amount of more than about 10% w/w and less than about 25% w/w (i.e. a high-dose, non-placebo challenge meal formulation);

wherein the placebo challenge meal formulation comprises an additive present in an amount of up to about 1.5% w/w of the oral food challenge meal formulation, wherein the additive is selected from the group consisting of: maltodextrin, dextrin, cyclodextrin and combinations thereof.

The kits of the present invention differ from conventional kits in that the placebo formulation includes an additive selected from the group consisting of: maltodextrin, dextrin, cyclodextrin and combinations thereof. Thus, the original formulation developed for the EuroPrevall project[8] has been modified to allow inclusion of increased amounts of allergenic ingredient whilst maintaining blinding (e.g. texture and/or taste blinding). A key aspect of the new invention is being able to manipulate the texture of the placebo and active doses to enable them to be matched.

In accordance with the present invention there is provided a method of diagnosing a food allergy comprising:
- a) administering to a subject a challenge meal formulation of the invention comprising no food allergen (a placebo challenge meal formulation); or a challenge meal formulation of the invention comprising allergen present in the challenge meal formulation in an amount of more than about 10% w/w and less than about 25% w/w (i.e. a high-dose, non-placebo challenge meal formulation), wherein the presence or absence of food allergen in the challenge meal formulation is not known to the subject;
- b) monitoring for an allergic response;
- c) grading the allergic response;
- d) repeating steps a) to c) with a different challenge meal formulation until all challenge meal formulations have been administered;
- e) correlating the graded allergic response with the known level of food allergen; and
- f) diagnosing whether or not the subject has a food allergy.

In accordance with the present invention there is provided a use of an additive in a placebo challenge meal formulation of a kit comprising a placebo dose formulation and a high-dose, non-placebo dose formulation comprising an allergen present in the challenge meal formulation in an amount of more than about 10% w/w and less than about 25% w/w, wherein the additive is selected from the group consisting of maltodextrin, dextrin, cyclodextrin and combinations thereof, the use being to make the placebo dose formulation indistinguishable from the high-dose, non-placebo dose formulation.

DETAILED DESCRIPTION OF THE DISCLOSURE

Figure 1:
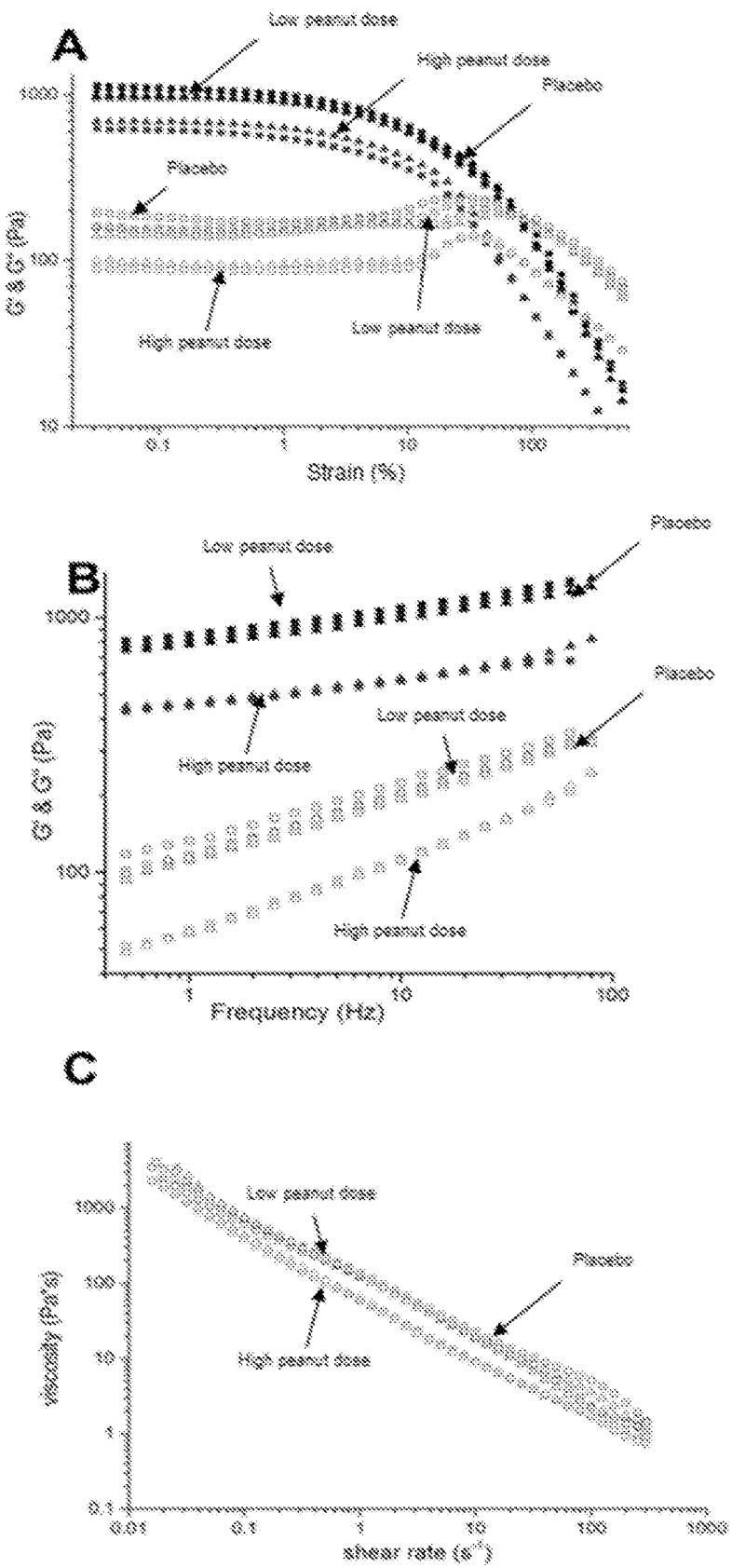
FIG. 1: Oscillatory rheology showing (A) Dynamic strain sweep plots; (B): Dynamic frequency plots; (C) Flow sweep for placebo, low peanut and high peanut doses in conventional EuroPrevall chocolate dessert matrix formulations. In panels (A) and (B) the closed symbols represent G' and open symbols G" measurements respectively whilst triangles and squares represent replicate measurements made on two different pots of reconstituted challenge meal. Low peanut dose, high peanut dose and placebo formulations are annotated on the plots

Kits Comprising Placebo and Non-Placebo Oral Food Challenge Meal Formulations:

In accordance with the present invention there is provided a kit comprising:
a challenge meal formulation comprising no food allergen (i.e. a placebo challenge meal formulation); and
a challenge meal formulation comprising allergen, wherein the allergen is present in the challenge meal formulation in an amount of more than about 10% w/w and less than about 25% w/w (i.e. a high-dose, non-placebo challenge meal formulation);
wherein the placebo challenge meal formulation comprises an additive present in an amount of up to about 1.5% w/w of the oral food challenge meal formulation, wherein the additive is selected from the group consisting of: maltodextrin, dextrin, cyclodextrin and combinations thereof.

In an embodiment, the kit of the present invention comprises: (i) a challenge meal formulation comprising no food allergen, wherein the challenge meal formulation comprises from about 0.05% w/w to about 1.5% w/w additive; and (ii) a challenge meal formulation comprising more than 10% w/w and less than about 25% w/w of allergen. Preferably, the presence or absence of food allergen in the challenge meal formulation is not known to the subject.

In an embodiment, the high-dose allergen formulations include formulations having more than about 10% w/w to about 25% w/w; more than about 10 w/w to about 24% w/w; more than about 10 w/w to about 23% w/w; more than about 10 w/w to about 22% w/w; more than about 10 w/w to about 21% w/w; more than about 10 w/w to about 20% w/w; more than about 10% w/w to about 19% w/w; more than about 10% w/w to about 18% w/w; more than about 10% w/w to about 17% w/w; more than about 10% w/w to about 16% w/w; or more than about 10% w/w to about 15% w/w allergen component.

In an embodiment, the high-dose allergen formulations include formulations having more than about 10% w/w to about 25% w/w; more than about 11 w/w to about 25% w/w; more than about 12 w/w to about 25% w/w; more than about 13 w/w to about 25% w/w; more than about 14 w/w to about 25% w/w; more than about 15 w/w to about 25% w/w; more than about 16% w/w to about 25% w/w; more than about 17% w/w to about 25% w/w; more than about 18% w/w to about 25% w/w; more than about 19% w/w to about 25% w/w; or more than about 20% w/w to about 25% w/w allergen component.

In line with the teaching of the present invention, in a kit comprising a placebo dose formulation and a high-dose, allergen containing formulation, the presence of the additive in the placebo dose formulation matches the texture of this formulation with the texture of the high-dose allergen containing formulation (such that the placebo and high-dose allergen containing formulation are indistinguishable).

In accordance with the present invention there is provided a kit of the present invention for use in diagnosing a food allergy.

In an embodiment, the challenge meal formulation of the kit of the invention further comprises: a matrix formation component; a texturizing component (i.e. a texture compensating component); and a flavour/colour masking component. The additive component (i.e. the maltodextrin, dextrin and/or cyclodextrin) component of the challenge meal formulation of the kit of the invention may be, but is not necessarily, described as being a part of the texture compensatory component.

Formulations comprising an allergen component are non-placebo formulations. Formulations not including an allergen component are placebo formulations.

Additive Component (i.e. Maltodextrin, Dextrin and/or Cyclodextrin Component):

In an embodiment, the additive component is present in the placebo challenge meal formulation in an amount of no more than about 1.5% w/w; no more than about 1.4% w/w; no more than about 1.3% w/w; no more than about 1.2% w/w; no more than about 1.1% w/w; no more than about 1.0% w/w; no more than about 0.9% w/w; no more than about 0.8% w/w; no more than about 0.7% w/w; no more than about 0.6% w/w; or no more than about 0.5% w/w.

In an embodiment, the additive component is present in the placebo challenge meal formulation in an amount of more than 0.05% w/w. In an embodiment, the additive component is present in the placebo challenge meal formulation in an amount of more than 0.1% w/w.

In an embodiment, the additive component is also present in the non-placebo challenge meal formulation. In an embodiment, the additive component is also present in the non-placebo challenge meal formulation in an amount of no more than about 1.5% w/w; no more than about 1.4% w/w; no more than about 1.3% w/w; no more than about 1.2% w/w; no more than about 1.1% w/w; no more than about 1.0% w/w; no more than about 0.9% w/w; no more than about 0.8% w/w; no more than about 0.7% w/w; no more than about 0.6% w/w; or no more than about 0.5% w/w. In an embodiment, the additive component is also present in the non-placebo challenge meal formulation in an amount of more than 0.05% w/w. In an embodiment, the additive component is also present in the non-placebo challenge meal formulation in an amount of more than 0.1% w/w.

Preferably, the additive component is present in the placebo challenge meal formulation in an amount of from about 0.05% w/w to about 1.5% w/w. More preferably, the additive component is present in the placebo challenge meal formulation in an amount of from about 0.05% w/w to about 1.0% w/w. More preferably, the additive component is present in the placebo challenge meal formulation in an amount of from about 0.05% w/w to about 0.5% w/w. The additive component may be present in the placebo challenge meal formulation in an amount of from about 0.05% w/w to about 0.4% w/w, from about 0.05% w/w to about 0.3% w/w, from about 0.1% w/w to about 0.5% w/w or from about 0.2% w/w to about 0.5% w/w.

The additive component may also be present in the non-placebo challenge meal formulation in an amount of from about 0.05% w/w to about 1.5% w/w. The additive component may also be present in the non-placebo challenge meal formulation in an amount of from about 0.05% w/w to about 1.0% w/w. The additive component may also be present in the non-placebo challenge meal formulation in an amount of from about 0.05% w/w to about 0.5% w/w. The additive component may also be present in the non-placebo challenge meal formulation in an amount of from about 0.05% w/w to about 0.4% w/w, from about 0.05% w/w to about 0.3% w/w, from about 0.1% w/w to about 0.5% w/w or from about 0.2% w/w to about 0.5% w/w.

The amount of additive component in the placebo challenge meal formulation is important as this is determinate of the texture of the formulation (e.g. by the degree of emulsification, stability and/or homogeneity of the formulation).

In an embodiment, the high-dose allergen formulation includes substantially no additive. In an embodiment, the high-dose allergen formulation includes 0% w/w additive.

In an embodiment, the additive component comprises maltodextrin. In an alternate embodiment, the additive component comprises dextrin. In an alternate embodiment, the additive component comprises cyclodextrin.

Preferably the additive component comprises maltodextrin. Preferably, the maltodextrin is present in the formulation, e.g. the non-placebo formulation, in an amount of from about 0.05% w/w to about 0.5% w/w.

Matrix Formation Component:

In an embodiment, the matrix formation component is present in the formulation in an amount of from about 20% w/w to about 60% w/w; from about 25% w/w to about 55% w/w; or from about 30% w/w to about 50% w/w.

In an embodiment, the matrix formation component comprises a starch component and sucrose.

In an embodiment, the starch component of the matrix formation component comprises a cold swelling starch or a pregelatinised modified starch. Preferably, a cold swelling starch as cold hydrating viscosifying agent is employed as the starch component of the matrix formation component. In a preferred embodiment of the cold swelling starch is selected from the group consisting of: Ultratex 2™, Ultratex 2000™, Ultratex 3™, Ultratex 4™, Ultratex SR™, Ultratex HV™, Instant Clearjel™, Ultrasperse 3™, Ultrasperse™ IMF, Ultrasperse 5™, Ultrasperse A™, NOVATION Endura 0100, NOVATION Prima 300, NOVATION 8300, NOVATION 3300, NOVATION 9230, NOVATION 9330, and combinations thereof. Most preferably the starch component of the matrix formation component is Ultratex 4™. The mentioned examples are available from Ingredion.

In an embodiment, the starch component is present in the formulation in an amount of from about 10% w/w to about 25% w/w. The starch component may be present in the formulation in an amount of from about 10% w/w to about 24% w/w, from about 10% w/w to about 23% w/w, from about 10% w/w to about 22% w/w, from about 10% w/w to about 21% w/w, from about 10% w/w to about 20% w/w or from about 10% w/w to about 19% w/w. The starch component may be present in the formulation in an amount of from about 11% w/w to about 25% w/w, from about 12% w/w to about 25% w/w, from about 13% w/w to about 25% w/w or from about 14% w/w to about 25% w/w. Preferably, the starch component is present in the formulation in an amount of from about 14% w/w to about 19% w/w.

In an embodiment, the sucrose component is present in the formulation in an amount of from about 15% w/w to about 30% w/w. The sucrose component may be present in the formulation in an amount of from about 15% w/w to about 29% w/w, from about 15% w/w to about 28% w/w, from about 15% w/w to about 27% w/w or from about 15% w/w to about 26% w/w. The sucrose component may be present in the formulation in an amount of from about 16% w/w to about 30% w/w, from about 17% w/w to about 30% w/w, from about 18% w/w to about 30% w/w or from about 19% w/w to about 30% w/w. Preferably, the sucrose component is present in the formulation in an amount of from about 18% w/w to about 28% w/w. More preferably, the sucrose component is present in the formulation in an amount of from about 18% w/w to about 27% w/w.

Preferably the matrix formation component comprises sucrose and Ultratex 4™. Preferably, the sucrose is present in the formulation in an amount of from about 18% w/w to about 26% w/w and the Ultratex 4™ is present in the formulation in an amount of from about 14% w/w to about 19% w/w.

Texturizing Component:

As mentioned above, the additive component (i.e. the maltodextrin, dextrin and/or cyclodextrin) component of the formulation may be, but is not necessarily, described as being a part of the texturizing component (i.e. texture compensatory component).

In an embodiment, the texturizing component is present in the formulation in an amount of from about 10% w/w to about 35% w/w; from about 15% w/w to about 30% w/w; or from about 20% w/w to about 25% w/w.

In an embodiment, the texturizing component comprises an oil component and a surfactant.

In an embodiment, the oil component of the texturizing component comprises a fat or fat blends selected from the group consisting of: highly refined, bleached and deodorised oils. Preferably, the oil component of the texturizing component is selected from the group consisting of: maize oil, sunflower oil, rapeseed oil, corn oil, low melting fats and combinations thereof. In an embodiment, the oil component of the texturising component is a non-allergenic species and of non-dairy origin. Preferably, the oil component of the texturizing component comprises highly refined oil or maize oil.

In an embodiment, the oil component is present in the formulation in an amount of from about 15% w/w to about 30% w/w. The oil component may be present in the formulation in an amount of from about 15% w/w to about 29% w/w, from about 15% w/w to about 28% w/w, from about 15% w/w to about 27% w/w, from about 15% w/w to about 26% w/w or from about 15% w/w to about 25% w/w. The oil component may be present in the formulation in an amount of from about 16% w/w to about 30% w/w, from about 17% w/w to about 30% w/w, from about 18% w/w to about 30% w/w, from about 19% w/w to about 30% w/w or about 20% w/w to about 30% w/w. Preferably, the oil component is present in the formulation in an amount of from about 20% w/w to about 25% w/w. More preferably, the oil component is present in in the formulation in an amount of from about 21% w/w to about 24% w/w. Still more preferably, the oil component is present in in the formulation in an amount of from about 22% w/w to about 24% w/w. Most preferably, the oil component is present in in the formulation in an amount of from about 22% w/w to about 23% w/w.

In an embodiment, the surfactant component of the texturizing component is selected from the group consisting of: lecithin, polyglycerol polyricinoleate, monoglycerides, distilled monoglycerides, citric acid esters of monoglycerides, di-acetyl acetic acid esters of monoglycerides, lactic acid esters of monoglyceride, diglycerides, polyglycerol esters of fatty acids or sorbitan esters of fatty acids and polyoxyethylene compositions such as sorbitan monopolyoxyethylene (Tween). Preferably, the surfactant component of the texturizing component is selected from the group consisting of: lecithin and a polyoxyethylene composition, such as sorbitan monopolyoxyethylene (Tween). Most preferably, the surfactant component of the texturizing component is Polysorbate 60 (e.g. Tween 60).

In an embodiment, the surfactant component is present in the formulation in an amount of from about 0.1% w/w to about 2% w/w. The surfactant component may be present in the formulation in an amount of from about 0.1% w/w to about 1.8% w/w, from about 0.1% w/w to about 1.6% w/w, from about 0.1% w/w to about 1.4% w/w, from about 0.1% w/w to about 1.2% w/w or from about 0.1% w/w to about 1.0% w/w. The surfactant component may be present in the formulation in an amount of from about 0.2% w/w to about 2% w/w, from about 0.3% w/w to about 2% w/w, from about 0.4% w/w to about 2% w/w or from about 0.5% w/w to about 2% w/w. Preferably, the surfactant component is present in the formulation in an amount of from about 0.5% w/w to about 1.0% w/w. More preferably, the surfactant component is present in the formulation in an amount of from about 0.5% w/w to about 0.9% w/w. Still more preferably, the surfactant component is present in the formulation in an amount of from about 0.5% w/w to about 0.8% w/w. Yet still more preferably, the surfactant component is present in the formulation in an amount of from about 0.5% w/w to about 0.7% w/w. Most preferably, the surfactant component is present in the formulation in an amount of from about 0.5% w/w to about 0.6% w/w.

Preferably the texturizing component comprises Polysorbate 60 and highly refined oil or maize oil. Preferably, the Polysorbate 60 is present in the formulation in an amount of from about 0.5% w/w to about 0.6% w/w and the highly refined oil or maize oil is present in the formulation in an amount of from about 22% w/w to about 23% w/w.

Flavour/Colour Masking Component:

In an embodiment, the flavour/colour masking component is present in the formulation in an amount of from about 10% w/w to about 45% w/w; from about 15% w/w to about 40% w/w; or from about 20% w/w to about 35% w/w.

In an embodiment, the flavour/colour masking component comprises a highly coloured food powder, a grain component and a liquid (e.g. oil) or powder based flavouring selected from the group consisting of: banana, pineapple, cherry, blackcurrant, raspberry, strawberry, blackberry, blueberry, cranberry, plum, coconut, guava, red apple, pear, mango, apricot, peach, chocolate, cocoa, caramel, toffee, molasses, condensed milk, butterscotch, buttery, bubble gum, fudge, cotton candy, vanilla, coffee, cinnamon, ice cream, honey, custard and combinations thereof.

In an embodiment, the highly coloured food powder of the flavour/colour masking component is selected from the group consisting of: cocoa, tomato, beetroot, carrot and carob powders. Preferably, the highly coloured food powder of the flavour/colour masking component is cocoa or tomato powder. Most preferably, the highly coloured food powder of the flavour/colour masking component is cocoa powder. In an embodiment, the highly coloured food powder of the flavour/colour masking component is a highly coloured sweet food powder of the flavour/colour masking component.

In an embodiment, the highly coloured food powder is present in the formulation in an amount of from about 15% w/w to about 30% w/w. The highly coloured food powder may be present in the formulation in an amount of from about 15% w/w to about 29% w/w, from about 15% w/w to about 28% w/w, from about 15% w/w to about 27% w/w, from about 15% w/w to about 26% w/w or from about 15% w/w to about 25% w/w. The highly coloured food powder may be present in the formulation in an amount of from about 16% w/w to about 30% w/w, from about 17% w/w to about 30% w/w, from about 18% w/w to about 30% w/w or from about 19% w/w to about 30% w/w. Preferably, the highly coloured food powder is present in the formulation in an amount of from about 19% w/w to about 25% w/w.

In an embodiment, the grain component is present in the formulation in an amount of from about 1% w/w to about 10% w/w. The grain component may be present in the formulation in an amount of from about 1% w/w to about 9% w/w, from about 1% w/w to about 8% w/w or from about 1% w/w to about 7% w/w. The grain component may be present in the formulation in an amount of from about 2% w/w to about 10% w/w or from about 3% w/w to about 10% w/w. Preferably, the grain component is present in the formulation in an amount of from about 3% w/w to about 8% w/w.

In an embodiment, the grain component is selected from the group consisting of: oatmeal, an edible member of the Poaceae such as the Triticeae family grain (e.g. wheat, barley or spelt), Pryzea (e.g. rice) or Panicoideae (e.g. maize). Preferably, the grain component is oatmeal. In an embodiment, the oatmeal is toasted oatmeal. In an embodiment, the oatmeal is ground oatmeal. Ground oatmeal is prepared by milling the oatmeal to a particle size of about 0.1 to 1 mm, preferably 0.3 to 0.8 mm and most preferably about 0.5 mm. In an embodiment, the oatmeal is toasted and ground oatmeal. Toasted and ground oatmeal (prepared by toasting fine oatmeal and then milling about 0.5 mm) yields a fine, hard and gritty meal which has a sweet and nutty flavour. This component is particularly useful in challenge meal formulations including peanut allergen.

In an embodiment, the liquid or powder based flavouring is present in the formulation in an amount of from about 0.1% w/w to about 3% w/w; from about 0.3% w/w to about 2.5% w/w; or from about 0.5% w/w to about 2.0% w/w. The liquid or powder based flavouring may be present in the formulation in an amount of from about 0.1% w/w to about 2.4% w/w; from about 0.1% w/w to about 2.3% w/w; from about 0.1% w/w to about 2.2% w/w; from about 0.1% w/w to about 2.1% w/w; from about 0.1% w/w to about 2.0% w/w; from about 0.1% w/w to about 1.9% w/w; or from about 0.1% w/w to about 1.8% w/w. The liquid or powder based flavouring may be present in the formulation in an amount of from about 0.2% w/w to about 2.5% w/w; from about 0.3% w/w to about 2.5% w/w; from about 0.4% w/w to about 2.5% w/w; from about 0.5% w/w to about 2.5% w/w; from about 0.6% w/w to about 2.5% w/w; from about 0.7% w/w to about 2.5% w/w; or from about 0.8% w/w to about 2.5% w/w. Preferably, the liquid or powder based flavouring is present in the formulation in an amount of from about 0.8% w/w to about 1.8% w/w.

In an embodiment, the liquid or powder based flavouring comprises a chocolate flavoured powder. In an embodiment, the liquid or powder based flavouring comprises a chocolate flavoured powder in combination with one or more of the liquid or powder based flavourings mentioned above.

Preferably the flavour/colour masking component comprises cocoa powder, oatmeal and a liquid or powder based flavouring. Preferably, the cocoa powder is present in the formulation in an amount of from about 19% w/w to about 25% w/w, the oatmeal is present in the formulation in an amount of from about 3% w/w to about 8% w/w and the liquid or powder based flavouring is present in the formulation in an amount of from about 0.8% w/w to about 1.8% w/w. Preferably the oatmeal is toasted and ground oatmeal.

Allergen Component:

In formulations comprising an allergen component the allergen component is present in the formulation in an amount of more than about 10% w/w and less than about 25% w/w. It has surprisingly been found in triangle testing experiments that formulations containing larger quantities of allergen component can be masked in terms of taste and/or texture. To date, triangle testing experiments of kits including a placebo component and a high-dose (e.g. 20% w/w allergen dose) had not yielded results indicating successful masking of a high-dose allergen component relative to the placebo component of the kit.

In an embodiment, the allergen component is selected from the group consisting of: legumes (such as peanut, soy, lupin), egg, milk (e.g. cows milk), fish, crustaceans, tree nuts and nut-like seeds (such as almond, cashew, hazelnut, pistachio, walnut, pecan, Brazil nut), sulphites, wheat, other seeds and grains such as mustard, sesame wheat, vegetables, such as celery (celeriac) or fruits, such as apple and peach allergen. In a preferred embodiment, the allergen component is peanut allergen.

In an embodiment, the kit further comprises (in addition to the placebo and high-dose formulation) a low-dose allergen formulation. In an embodiment, the allergen component in the low-dose allergen formulation is present in the formulation in an amount of from about 0.5% w/w to about 10% w/w, preferably from about 1% w/w to about 10% w/w.

In an embodiment, the allergen component in the low-dose allergen formulation is present in the formulation in an amount of from about 1% w/w to about 9% w/w; about 1% w/w to about 8% w/w; about 1% w/w to about 7% w/w; about 1% w/w to about 6% w/w; about 1% w/w to about 5% w/w; about 1% w/w to about 4% w/w; about 1% w/w to about 3% w/w; or about 1% w/w to about 2% w/w allergen component.

Method of Diagnosing a Food Allergy:

In accordance with the present invention there is provided a method of diagnosing a food allergy comprising:
 a) administering to a subject a challenge meal formulation of the invention comprising (i) no food allergen (a placebo challenge meal formulation); or (ii) a challenge meal formulation of the invention comprising allergen present in the challenge meal formulation in an amount of more than about 10% w/w and less than about 25% w/w (i.e. a high-dose, non-placebo challenge meal formulation, wherein the presence or absence of food allergen in the challenge meal formulation is not known to the subject;
 b) monitoring for an allergic response;
 c) grading the allergic response;
 d) repeating steps a) to c) with a different challenge meal formulation until all challenge meal formulations have been administered;
 e) correlating the graded allergic response with the known level of food allergen; and
 f) diagnosing whether or not the subject has a food allergy.

In an embodiment, step (a) of the method further comprises administering to the subject a low-dose allergen formulation. In an embodiment, the allergen component in the low-dose allergen formulation is present in the formulation in an amount of from about 0.5% w/w to about 10% w/w, preferably from about 1% w/w to about 10% w/w. In an embodiment, the allergen component in the low-dose allergen formulation is present in the formulation in an amount of from about 1% w/w to about 9% w/w; about 1% w/w to about 8% w/w; about 1% w/w to about 7% w/w; about 1% w/w to about 6% w/w; about 1% w/w to about 5% w/w; about 1% w/w to about 4% w/w; about 1% w/w to about 3% w/w; or about 1% w/w to about 2% w/w allergen component.

The presence of the additive is particularly important in formulations containing no allergen (i.e. placebo dose formulations) and low-dose allergen formulations (i.e. non-placebo, low dose formulations). Thus, in an embodiment, step (a) of the method of diagnosing a food allergy comprises administering to a subject (i) a challenge meal formulation of the invention comprising no food allergen, wherein the challenge meal formulation comprises from about 0.05% w/w to about 1.5% w/w additive; (ii) a challenge meal formulation of the invention comprising a low dose (e.g. about 1% w/w to about 10% w/w) of allergen, wherein the challenge meal formulation comprises from about 0.05% w/w to about 1.5% w/w additive; or (iii) a challenge meal formulation of the invention comprising a high dose (e.g. more than about 10% w/w to about 25% w/w) of allergen, wherein the challenge meal formulation comprises 0% w/w additive, wherein the presence or absence of food allergen in the challenge meal formulation is not known to the subject.

Definitions

For the avoidance of doubt, it is hereby stated that the information disclosed earlier in this specification under the heading "Background" is relevant to the invention and is to be read as part of the disclosure of the invention.

Throughout this specification, whenever a specific value is quoted for a temperature, pressure or time, the temperature, pressure or time quoted is approximate rather than the precise temperature, amount of pressure or amount of time. Nevertheless, the disclosure includes the precise value of any such variables which are approximately that value.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCES

1 Bock, S. A. et al. Double-blind, placebo-controlled food challenge (DBPCFC) as an office procedure: a manual. *The Journal of allergy and clinical immunology* 82, 986-997 (1988).
2 Ingelfinger, F. J., Lowell, F. C. & Franklin, W. Gastrointestinal allergy. *The New England journal of medicine* 241, 337; passim, doi:10.1056/nejm194909012410905 (1949).
3 Niggemann, B. & Beyer, K. Pitfalls in double-blind, placebo-controlled oral food challenges. *Allergy* 62, 729-732, doi:10.1111/j.1398-9995.2007.01396.x (2007).
4 Sampson, H. A. et al. Standardizing double-blind, placebo-controlled oral food challenges: American Academy of Allergy, Asthma & Immunology-European Academy of Allergy and Clinical Immunology PRACTALL consensus report. *The Journal of allergy and clinical immunology* 130, 1260-1274, doi:10.1016/j.jaci.2012.10.017 (2012).
5 Vassilopoulou, E. et al. Evaluation and standardisation of different matrices used for double-blind placebo-controlled food challenges to fish. *Journal of human nutrition and dietetics: the official journal of the British Dietetic Association* 23, 544-549, doi:10.1111/j.1365-277X.2010.01046.x (2010).
6 Vlieg-Boerstra, B. J. et al. Development and validation of challenge materials for double-blind, placebo-controlled food challenges in children. *The Journal of allergy and clinical immunology* 113, 341-346, doi:10.1016/j.jaci.2003.10.039 (2004).
7 Ronteltap, A. et al. Sensory testing of recipes masking peanut or hazelnut for double-blind placebo-controlled food challenges. *Allergy* 59, 457-460 (2004).
8 Cochrane, S. A. et al. Development of a standardized low-dose double-blind placebo-controlled challenge vehicle for the EuroPrevall project. *Allergy* 67, 107-113, doi:10.1111/j.1398-9995.2011.02715.x (2012).
9 Mackie, A. et al. High fat food increases gastric residence and thus thresholds for objective symptoms in allergic patients. *Molecular nutrition & food research* 56, 1708-1714, doi:10.1002/mnfr.201200330 (2012).
10 Ballmer-Weber, B. K. et al. How much is too much? Threshold dose distributions for 5 food allergens. *The Journal of allergy and clinical immunology* 135, 964-971, doi:10.1016/j.jaci.2014.10.047 (2015).

EXAMPLES

The following examples provide various formulations falling within the scope of the present invention.

There is a fine balance between the amount of starch, maltodextrin, polysorbate, and maize oil which will determine the degree of emulsification and thus stability and homogeneity of the mixture.

The matrix formation is driven by the ability of Ultratex 4 (Starch, hydrogen phosphate, 2-hydroxypropyl ether, CAS 53124-00-8) to form a gel network on addition of water. The key aspect of the invention is the manipulation of the rheological properties of the gel network by the addition of maltodextrin in the placebo formulation to allow textural matching with the active.

Sensory properties of the following formulations have been evaluated by informal taste panels (n=4-8) to assess blinding with regards to texture. Attributes scored were identified regarding the organoleptic properties of the dessert. Little difference was perceived with regards odour and flavour attributes between the placebo and allergen containing formulations, including roasted nut flavours. Importantly, no trace of peanut could be discerned in the allergen containing formulations. With regards the texture, no difference in the thickness of the desserts was perceived and little variation in its smoothness, grittiness or astringent qualities could be discerned.

Example 1

The formulation comprises the following ingredients:

| | Placebo formulation (% w/w) | Peanut containing formulation (% w/w) |
|---|---|---|
| Peanut Flour | 0.00 | 20 |
| Maltodextrin | 0.50 | 0 |
| Starch (Ultra-TEX-4) | 17.00 | 14.23 |
| Toasted Oatmeal | 7.67 | 3.34 |
| Alkalised Cocoa | 24.26 | 19.15 |
| Sucrose | 26.05 | 18.74 |
| Maize oil | 22.83 | 22.00 |
| Polysorbitan 60 | 0.60 | 0.60 |
| Fruit flavours | 1.09 | 1.94 |
| Total | 100.00 | 100.00 |

Example 2: Sensory Evaluation of Chocolate Mousse Containing Peanut Protein Using the Triangle Test Method for Similarity In order to diagnose the severity of a peanut allergy, a chocolate mousse product (with different peanut levels) was produced (in line with the formulations of Example 1). Two samples of chocolate mousse: "Control" (placebo recipe containing no peanut protein) and "Test" (a recipe containing peanut at 20% w/w) were submitted for sensory evaluation using the Triangle Test Method TES-S-001 (for similarity) using a panel of 42 sensory assessors (selected from the Campden BRI Trained Triangle Test Panel).

The samples were submitted as a concentrated dessert format. Prior to the test the samples were prepared by reconstitution with cold water (mains supply) by the following protocol:

Pots were stored at ambient temperature (25° C.), and out of direct sun light prior to reconstitution.

The dessert doses were produced in 300 g masses in 800 ml pots.

Each 300 g doses were reconstituted as a single dose.

Reconstitution was carried out with all placebo desserts first followed by all the peanut containing doses.

Water from the mains supply at Campden BRI was used to reconstitute.

After initial reconstitution the desserts were stored in a refrigerator between 2-8° C. overnight.

700 mls of water was measured out using a measuring jug.

100 mls of the measured water was poured into the pot containing the dry dessert and mixed with the spatula until fully absorbed.

The pots were then left at room temperature for 10 minutes.

The dessert was emptied into a Kenwood mixer (model number: Major KM230) with a paddle blade.

The remaining 600 mls of water was poured into the now empty dessert pot and residual dessert was dissolved by gentle mixing.

The desert matrix was them mixed on low speed for 2 minutes.

A further 100 mls of water was added and mixed on low speed for 2 minutes.

A third 100 mls of water was added and mixed on low speed for 2 minutes.

Then 200 mls of water was added and mixed on low speed for 2 minutes.

The remaining water was added and mixed on low speed for 2 minutes.

The final reconstituted dessert was emptied into a coded glass mixing bowl, covered with tin foil and refrigerated overnight.

The above protocol was repeated for each pot working initially with placebo and then onto the peanut containing dose.

Between batches all equipment was washed with hot water and detergent and then rinsed with copious amounts of clean water. All equipment was then dried prior to use.

The aim of the test was to determine whether the panel could perceive any sensory difference(s) between the two samples to determine whether the addition of the peanut protein is detectable.

The samples were placed into the applicable coded containers presented following the experimental design of the test. Each assessor received a heaped teaspoon of sample per coded container.

The samples were evaluated using the Triangle Test Procedure (TES-S-001). In the triangle test assessors are presented with a set of three coded samples, two of which are the same and one of which is different. The sets of samples are presented equally often in each of the six possible orders; this experimental design minimises any possible order and carryover effects.

Forty-two trained assessors are used for each test, twenty-one receiving "test" as the different sample and twenty-one receiving "control" as the different sample. After tasting the three samples in the designated order, each assessor is asked to select the "different" sample and to describe the difference(s) perceived.

The test was carried out in a purpose-built testing room. Each assessor was required to undertake the tests in an individual booth. The room was positively pressurised to minimise the entrance of external odours. Coloured lighting was used to mask any colour difference between the samples. The panel were instructed to palate cleanse with plain crackers and water (bottled) between the samples to minimise sample carry-over.

For a triangle test for similarity using 42 assessors, a maximum number of 16 correct responses are required to establish similarity between the two samples. The results show that 10 of the 42 assessors correctly identified the odd or different sample. It can therefore be concluded that the samples are statistically similar at the 5% Beta ($\beta$) and 30% Pd selected levels, that is, we are 95% confident that only 30% of discriminators can detect a difference.

Alpha ($\alpha$)—probability of concluding that a perceptible difference exists when one does not Beta ($\beta$)—probability of concluding that no perceptible difference exists when one does Pd—maximum allowable proportion of distinguishers Reference: Sensory Analysis Methodology—Triangle Test BS EN ISO 4120: 2007

The test results above indicate that the two samples are statistically similar at the selected levels (5% Beta ($\beta$) and 30% Pd) i.e. no significant difference was detected between the two chocolate mousse samples: Test (20% w/w peanut recipe) and Control (placebo recipe).

Example 3: The Use of Maltodextrin in Texture Matching for Oral Food Challenge Meals Based on Cold Swelling Starch Conventional Formulations:

The EuroPrevall chocolate dessert matrix of the prior art was developed for diagnosis of food allergy by oral food challenge and is based on the chemically modified cold swelling starch Ultratex 4 [1, 2]. The challenge meals are made as a paste, comprising the cold swelling starch, oil, surfactant, together with the allergenic ingredient. Other ingredients, such as cocoa powder, sugar and flavours, are added to allow blinding of the colour and flavour of the added allergenic ingredient. The dessert is then reconstituted by addition of water prior to use.

In the development of oral food challenge meals it is important to match the texture of the placebo (no allergen) and high allergen doses. When levels greater than 13.3% (w/w) of allergenic ingredient in the dry base are added to the give the high dose, the proportion of cold swelling starch in the formulation is reduced as shown in the below Table. This adversely impacts on the gel formation and results in a difference in the rheological properties of the placebo and high peanut containing challenges. This is illustrated below for EuroPrevall formulation No 4:

Challenge Meal Dessert Base Formulation 4

| Ingredient | % (w/w) Ingredient in dessert base | | |
|---|---|---|---|
| | Placebo dessert | "Low-dose" peanut dessert | "High-dose" peanut dessert |
| Peanut Flour | 0.00 | 0.67 | 13.33 |
| Starch (Ultra-TEX-4) | 19.53 | 19.53 | 13.47 |
| Toasted Oatmeal | 6.67 | 6.00 | 3.34 |
| Cocoa powder | 18.33 | 18.33 | 18.33 |
| Sucrose | 30.74 | 30.74 | 26.60 |
| Maize oil | 23.33 | 23.33 | 23.33 |
| Polysorbitan 60 | 0.60 | 0.60 | 0.60 |
| Orange Oil | 0.80 | 0.80 | 1.00 |
| Total | 100 | 100 | 100 |

The rheological properties of the reconstituted high peanut dose showed significant deviations from the placebo and low peanut doses (FIG. 1). This resulted in perceptible differences in texture during sensory panel evaluation, which had to be addressed by reformulating the product.

Reformulation of Oral Food Challenges

Inclusion of higher levels of peanut flour to 17.5 and 20% (w/w of dry base) further increased the textural difference of the placebo and peanut containing challenge meals. During reformulation of the challenges it was discovered that addition of maltodextrin to the formulation affected the rheological properties of the reconstituted dessert. This was used as a means of manipulating the rheology of the placebo and low peanut doses to improve the texture matching with the high peanut (20% (w/w) of dry base). This gave rise to the recipe below.

Reacta Biotech Formulation [w/w (%)]

| | Placebo | Low dose peanut (0.67%) | High dose peanut (20%) |
|---|---|---|---|
| Peanut Flour | 0.00 | 0.67 | 20.00 |
| Maltodextrin | 0.50 | 0.50 | 0.00 |
| Starch (Ultra-TEX-4) | 17.00 | 17.00 | 14.23 |
| Toasted Oatmeal | 7.67 | 7.67 | 3.34 |
| Alkalised Cocoa | 24.26 | 23.54 | 19.15 |
| Sucrose | 26.35 | 26.29 | 18.89 |
| Maize oil | 22.83 | 22.83 | 22.00 |
| Polysorbitan 60 | 0.60 | 0.60 | 0.60 |
| Fruit flavours | 0.79 | 0.9 | 1.79 |
| Total | 100.00 | 100.00 | 100.00 |

The rheological properties of the above reformulated compositions were assessed by UNIMAN working in collaboration with the Edinburgh Complex Fluids Partnership.

Figure 2:
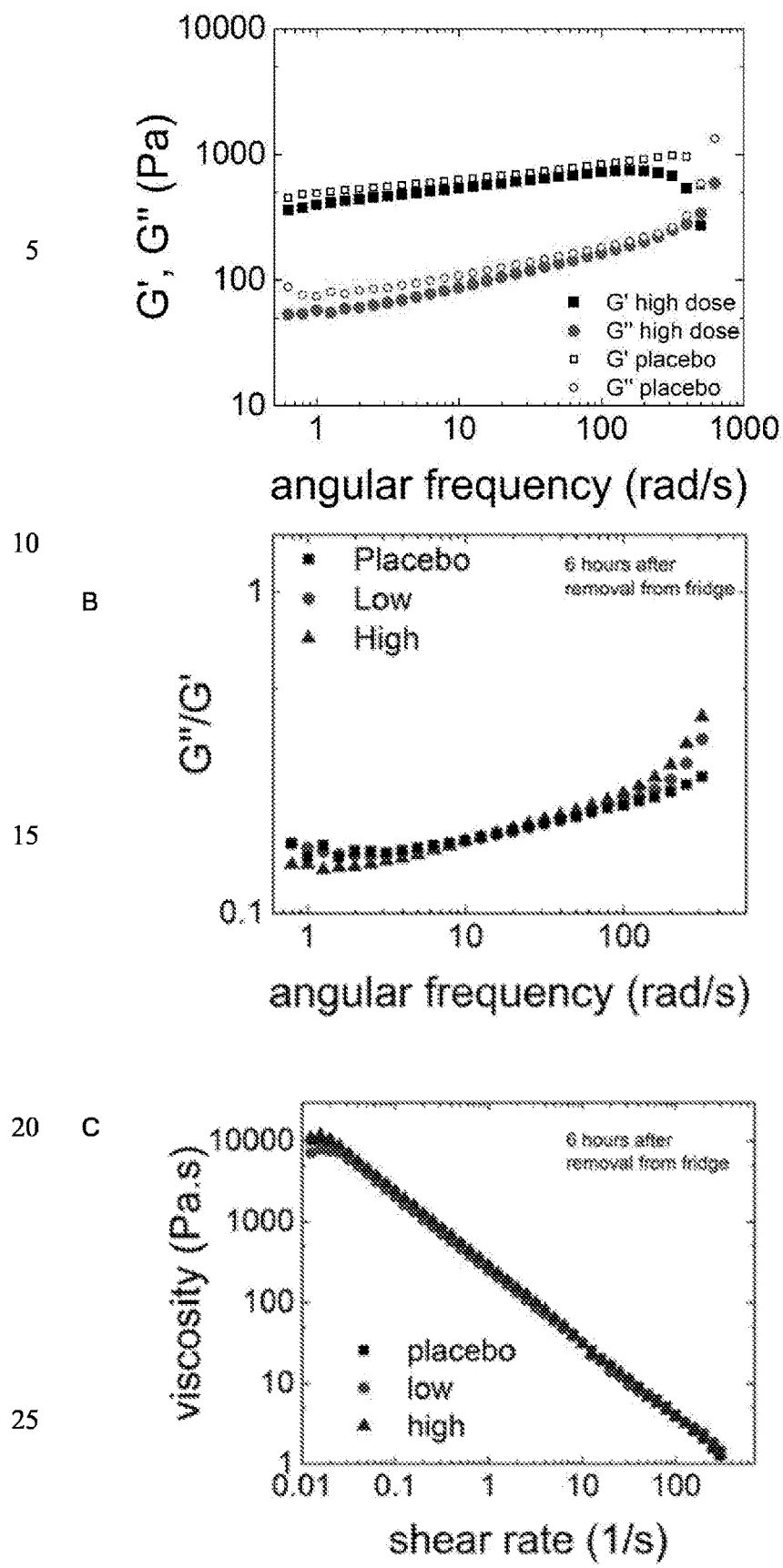
FIG. 2: Oscillatory rheology showing (A) Dynamic frequency plots (in which G' and G" are plotted separately) for the high dose and placebo reformulations; (B) Dynamic frequency tests (in which G' and G" are plotted as a ratio) for placebo (squares), low peanut (circles) and high peanut (triangles) dose reformulations; and (C) Flow sweep for placebo (squares), low peanut (circles) and high peanut (triangles) dose reformulations.

Data were obtained showing that on hydration the rheological properties of the placebo, low peanut dose and high peanut dose (containing 20% (w/w) in the dry base of peanut flour) were practically identical (FIGS. 2A, 2B and 2C) and much improved over the EuroPrevall Formulation 4 (FIGS. 1A, 1B and 1C).

The dynamic frequency test showed a slight deviation, with the rheology of the placebo being marginally less frequency dependent than the low peanut and high peanut flour meals. However for the flow sweeps no difference can be seen between the different doses when maltodextrin is included in the formulation.

The invention claimed is:

1. A kit comprising:
   a placebo challenge meal formulation comprising no food allergen; and
   a non-placebo challenge meal formulation comprising an allergen, wherein the allergen is present in the non-placebo challenge meal formulation in an amount of more than 10% w/w and less than 25% w/w;
   wherein the placebo and non-placebo challenge meal formulations each comprise:
   20% w/w to 60% w/w of a matrix formation component, wherein the matrix formation component comprises a starch and a sucrose;
   10% w/w to 35% w/w of a texturizing component, wherein the texturizing component comprises an oil component and a surfactant; and
   10% w/w to 45% w/w of a flavor/color masking component; and
   wherein the placebo challenge meal formulation comprises an additive present in an amount of from about 0.05% w/w to about 1.0 w/w of the placebo food challenge meal formulation, and wherein the additive is selected from the group consisting of: maltodextrin, dextrin, cyclodextrin and combinations thereof, and
   wherein, upon reconstitution with water, the placebo and the non-placebo challenge meal formulations each form a mousse.

2. The kit of claim 1, wherein the non-placebo challenge meal formulation comprises about 15% w/w to about 25% w/w of allergen.

3. The kit of claim 1, wherein the allergen is selected from the group consisting of: peanut, soy, egg, sesame seeds, milk, fish, crustaceans, almond, cashew, hazelnut, pistachio, walnut, sulphites, wheat, mustard and celery allergen.

4. The kit of claim 3, wherein the allergen is peanut allergen.

5. The kit of claim 1, wherein the additive is maltodextrin.

6. The kit of claim 1, wherein the starch component comprises a cold swelling starch or a pregelatinised modified starch.

7. The kit of claim 1, wherein the sucrose is present in an amount of from about 18% w/w to about 26% w/w and the starch component is present in an amount of from about 14% w/w to about 19% w/w.

8. The kit of claim 1, wherein the oil component of the texturizing component comprises highly refined oil or maize oil.

9. The kit of claim 1, wherein the surfactant component of the texturizing component is Polysorbate 60.

10. The kit of claim 1, wherein the surfactant is present in an amount of from about 0.5% w/w to about 0.6% w/w and the oil component is present in an amount of from about 22% w/w to about 23% w/w.

11. The kit of claim 1, wherein the flavor/color masking component comprises a highly colored food powder, a grain component and a liquid or powder based flavoring selected from the group consisting of: banana, pineapple, cherry, blackcurrant, raspberry, strawberry, blackberry, blueberry, cranberry, plum, coconut, guava, red apple, pear, mango, apricot, peach, chocolate, cocoa, caramel, toffee, molasses, condensed milk, butterscotch, buttery, bubble gum, fudge, cotton candy, vanilla, coffee, cinnamon, ice cream, honey, custard and combinations thereof.

12. The kit of claim 11, wherein the highly colored food powder is cocoa or tomato powder.

13. The kit of claim 11, wherein the grain component is oatmeal.

14. The kit of claim 11, wherein the liquid or powder based flavoring comprises a chocolate flavored powder.

15. The kit of claim 11, wherein the highly colored food powder is present in an amount of from about 19% w/w to about 25% w/w, the grain component is present in an amount of from about 3% w/w to about 8% w/w and the liquid or powder based flavoring is present in an amount of from about 0.8% w/w to about 1.8% w/w.

* * * * *